United States Patent [19]

Switalski et al.

[11] Patent Number: 5,047,350

[45] Date of Patent: Sep. 10, 1991

[54] MATERIAL AND METHOD FOR OXYGEN SENSING

[75] Inventors: Steven C. Switalski; Hsue-Yang Liu; Paul B. Merkel, all of Rochester; Bradley K. Coltrain, Fairport, all of N.Y.

[73] Assignee: Eastman Kodak Company, Rochester, N.Y.

[21] Appl. No.: 300,105

[22] Filed: Jan. 19, 1989

[51] Int. Cl.$^5$ .............................................. G01N 21/64
[52] U.S. Cl. .............................. 436/136; 250/459.1; 250/483.1; 422/56; 422/82.07; 422/82.08; 436/68; 436/138; 436/172
[58] Field of Search ................. 436/68, 136, 138, 172; 422/56-58, 82.05-82.08, 82.11; 250/459.1, 461.1, 461.2, 483.1; 128/633, 634

[56] References Cited

U.S. PATENT DOCUMENTS

| | | |
|---|---|---|
| 2,486,162 | 10/1949 | Hyde . |
| 3,725,658 | 4/1973 | Stanley et al. ................. 436/136 X |
| 4,238,590 | 12/1980 | Scholze et al. . |
| 4,587,101 | 5/1986 | Marsoner et al. . |
| 4,657,736 | 4/1987 | Marsoner et al. .................... 422/56 |
| 4,677,078 | 6/1987 | Minten et al. ....................... 436/136 |
| 4,849,172 | 7/1989 | Yafuso et al. .................. 436/138 X |

FOREIGN PATENT DOCUMENTS

| | | |
|---|---|---|
| 0091390 | 10/1983 | European Pat. Off. . |
| 0243116 | 10/1987 | European Pat. Off. . |
| 0244929 | 11/1987 | European Pat. Off. . |
| 0259951 | 3/1988 | European Pat. Off. . |
| 2132348 | 5/1987 | United Kingdom . |

OTHER PUBLICATIONS

Yilgor et al., *Advances in Polymer Science*, vol. 86, pp. 1-86, 1988.

Brinker, J. of Non Crystalline Solids, vol. 100, pp. 31-50, 1988.

The Merck Index, Tenth Edition, Edited by Windholz et al., Published by Merck & Co., Inc., 1983, pp. 1220-1221, #8331.

Avnir et al., Journal of Non-Crystalline Solids, 74, (1985), pp. 395-406.

Makishima et al., J. Am. Ceram. Soc., 69(4) c-72-C-74 (1986).

*Primary Examiner*—Robert J. Hill, Jr.
*Attorney, Agent, or Firm*—Robert A. Linn

[57] ABSTRACT

Silicic acid heteropolycondensates containing a luminescent compound, whose luminescence is quenchable by oxygen, form suitable sensors for measuring oxygen content in an oxygen-containing gaseous, liquid, or solid sample.

11 Claims, 8 Drawing Sheets

MATERIAL AND METHOD FOR OXYGEN SENSING

FIELD OF THE INVENTION

This invention relates to organic modified silicic acid heteropolycondensates and their use as membranes for passing oxygen. It also relates to their use in oxygen sensing.

BACKGROUND OF THE INVENTION

It is known that molecular oxygen will influence the intensity of luminescence of a large number of organic substances, e.g., polycyclic aromatic hydrocarbons. In such cases the molecular oxygen will interact with the molecule activated by the excitation light, drawing energy from the excited molecule and reducing the intensity of the fluorescent light emitted. It is also known that the Partial pressure of the molecular oxygen may be measured via the luminescence intensity of such an indicator substance. The luminescent material may be supplied in a solvent or embedded in a membrane. The partial pressure of the oxygen contained in the solvent or membrane will determine the degree of luminescence intensity.

This invention relates to membranes and films which are permeable to oxygen, and which are prepared from an organic modified silicic acid heteropolycondensate. Although certain heteropolycondensates of this type have been described in the art, it is believed that the advantageous oxygen permeability of such materials has not been previously discovered. It is also believed that these materials have not been previously employed for oxygen sensing.

RELATED ART

U.S. Pat. No. 2,486,162 discloses organic modified silicic acids of various types.

U.S. Pat. No. 4,238,590 describes other such materials useful as membranes and adsorbents.

British Patent 2,132,348B describes use of luminescent compounds in measuring oxygen concentration. The luminescent material is incorporated in a polymeric carrier which is permeable to oxygen. The purpose of the carrier is to prevent the luminescent substance from responding to contaminants and interferents. Polymers for such use are mentioned on page 8, lines 8–29.

U.S. Pat. No. 4,587,101 teaches that the suitability of a polymer for use as a membrane for $O_2$ determination mainly depends on its oxygen permeability, which should be sufficiently high. It also says that with the exception of silicone ($P_{O2} \approx 600 \times 10^{-10} cm^2 s^{-1} cmHg^{-1}$), the oxygen permeability of unplasticized polymers are too low ($P_{O2} < 35 \times 10^{-10} cm^2 s^{-1} cmHg^{-1}$) and do not yield useful results with regard to oxygen sensitivity, even if the fluorescence decay times of the indicator substances are long. Various polymer/plasticizer combinations are suggested, column 3, lines 1–40.

Avnir et al, *Journal of Non-Crystalline Solids* 74 (1985) 395–406, discloses the use of a sol/gel process to entrap organic fluorescent dyes in silica and silica-titania thin films. The heteropolycondensates are made by a polymerization/condensation reaction of metal alkoxides, followed by low temperature dehydration. Use of the films as solar or laser light guides is suggested.

Makishima et al, *J. Am. Ceram. Soc.* 69(4) c-72-c-74 (1986) discloses that molecular dispersions of amorphous silicious materials doped with organic molecules were prepared by a sol/gel Process in which Si-$(OC_2H_5)_4$ was hydrolyzed in neutral or acidic solution.

SUMMARY OF THE INVENTION

Organic modified silicic acid heteropolycondensates are useful for preparing membranes, coatings, and films which are permeable to oxygen. Compared with many organic polymeric substances, the heteropolycondensates used in this invention offer thermal stability and optical quality Properties of potential importance in optical oxygen sensors.

The oxygen permeability of the organic-inorganic polycondensates can be altered by utilizing different functional groups. Thus, the polycondensates offer an opportunity to "tailor make" or fine-tune a composition for use in a pre-selected application.

GLOSSARY

For the purpose of description of this invention, a shorthand notation has been adopted to describe various organic modified silicic and heteropolycondensates referred to herein. In the adopted notation system, the heteropolycondensates are identified by the relative percentages of monomers which were reacted to produce the condensate. Thus, for example, the designation "100 methyl" refers to an organic modified silicic acid heteropolycondensate made by the hydrolysis/condensation reaction (illustrated by Example 1) conducted using methyltriethoxysilane as the sole monomer. The notation "95-Phenyl/5-OSTEE" refers to a silicic acid heteropolycondensate made from a monomer mixture of 95 mole percent phenyltriethoxysilane and 5 mole % tetraethoxysilane. The adopted nomenclature is set forth in the following table:

| Adopted Nomenclature | |
|---|---|
| 100-methyl | 100% methyltriethoxysilane |
| 100-phenyl | 100% phenyltriethoxysilane |
| 100-octyl | 100% n-octyltriethoxysilane |
| phenyl(hyper) | hypercritically processed 100% phenyltriethoxysilane (see Example 2) |
| phenyl/propyl | commercial material made from a mixture of phenyl trialkoxysilane and n-propyltrialkoxysilane |
| 95-Phenyl/5-OSTEE | 95% phenyltriethoxysilane/ 5% tetraethoxysilane |
| 80-Phenyl/15-Ph$_2$/5-OSTEE | 80% phenyltriethoxysilane/ 15% dichlorodiphenylsilane/ 5% tetraethoxysilane |
| EC-C-18 | a silicic acid heteropolycondensate endcapped with octadecyldimethylchlorosilane |

Also, at various places within the following description of the invention, the silicic acid heteropolycondensates are referred to as "sol/gels".

The hydrolysis/condensation reaction employed to prepare the heteropolycondensates used in this invention can be illustrated by the following equations.

HYDROLYSIS

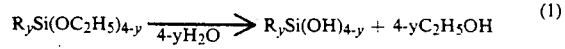

CONDENSATION $$RSi-OH + HO-Si-R \longrightarrow RSi-O-SiR + H_2O \quad (2)$$

When $y = 1$, Equation (1) illustrates complete hydrolysis of a triethoxysilane, such as phenyltriethoxysilane. As shown, for each molar equivalent of the trialkoxysilane which is completely hydrolyzed, three molar equivalents of water are consumed. The hydrolyzed product is comparatively unstable; it tends to rapidly undergo the condensation process illustrated by Equation (2). It is known in the art that condensation can begin to occur before all three alkoxide groups are hydrolyzed.

Equation (2) is an oversimplification. It illustrates condensation between two silanol groups, each of which were formed in step (1). As shown by the unsatisfied valences, further condensation between other groups can occur.

DESCRIPTION OF PREFERRED EMBODIMENTS

Figure 1:
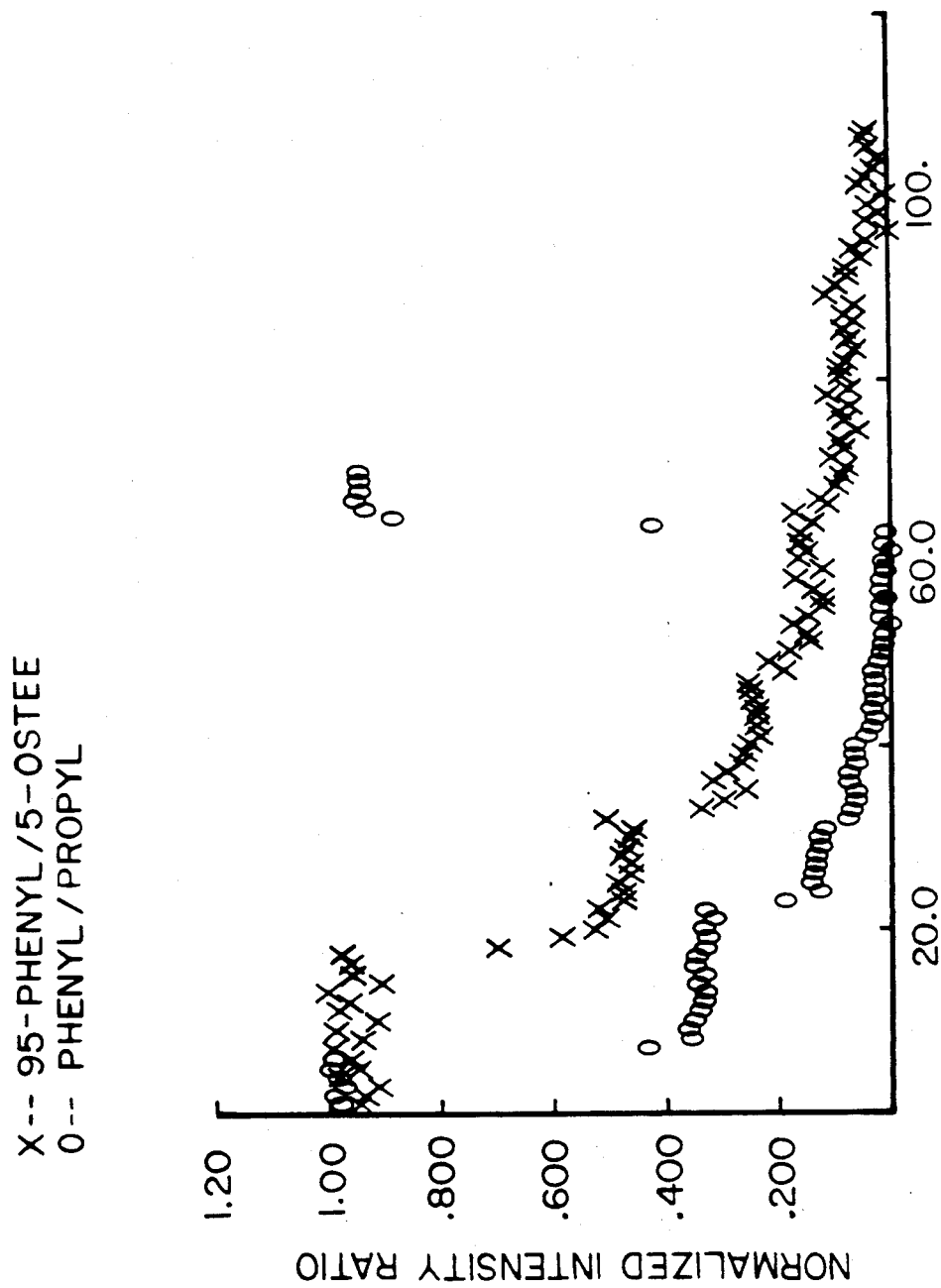
FIG. 1. The normalized phosphorescence intensities of PtOEP (platinum octaethylporphyrin) in (O) phenyl/propyl and (X) Ph/OSTEE coatings as a function of time. The oxygen partial pressure was changed in 5 steps from nitrogen to air.

This invention comprises a method of determining the presence of oxygen in a gaseous, liquid, or solid sample, said method comprising:

(A) exposing a sensor to said sample, said sensor comprising:
 (i) a luminescent material which luminesces when excited by visible or ultraviolet light and whose lifetime or intensity of luminescence is quenchable by oxygen, and
 (ii) a membrane which is permeable to oxygen and in which said luminescent material is embedded, (B) allowing oxygen from said sample to permeate said membrane and contact said luminescent material, (C) measuring the quench related decrease in luminescence caused by oxygen, and (D) using the measurement thereby obtained to determine the oxygen content of said sample;

said membrane consisting essentially of a silicic acid heteropolycondensate having silane units with the formula $RSi\equiv$, such that the free valences in said formula are interconnected by oxygen.

There are several types of heteropolycondensates which are preferred for us in this invention:

(1) Those wherein the R group in the silane units are selected from the class consisting of:
 (a) lower alkyl radicals having up to about 7 carbon atoms optionally substituted with halogen, e.g., fluorine;
 (b) aryl radicals having up to about 14 carbon atoms; and
 (c) mixtures of (a) and (b).

In one embodiment from about 70 to 100% of the R groups are selected from group (b) and 0-30% from group (a). In another embodiment the R radicals in the silane units are selected from subgroup (b), and the heteropolycondensate is further characterized by being substantially free of hydrolyzable groups or silanol groups.

(2) Those wherein the R radicals in said silane units are selected from alkyl groups having from about 7 to about 20 carbon atoms, optionally substituted with halogen, e.g., fluorine.

(3) Those wherein the R group in the silane units are alkyl radicals of up to about 20 carbon atoms (optionally substituted with halogen, e.g., fluorine) or aryl groups of up to about 14 carbon atoms with an amine radical $NR$, wherein $R_1$ and $R_2$ are alike or different, and selected from hydrogen and lower alkyl having up to about 4 carbon atoms. For example, the R group may be aminopropyl.

(4) Heteropolycondensates of classes (1), (2), or (3) above which have been subjected to a high temperature, high pressure treatment of the type illustrated by Example 2.

The process of this invention can also be carried out using an endcapped silicic acid condensate, i.e., a silicic acid heteropolycondensate having the repeating unit $Si\equiv$ wherein the unsatisfied valences in said units are interconnected by oxygen, and said condensate is endcapped by $R_3Si$-groups, wherein each R is alike or different and has the same significance as above. The condensates within this subclass (5) are illustrated by the non-limiting example, EC-C-18.

The heteropolycondensates used in this invention are made by causing molecules of one or more silanes selected from those having the formula:

$$\begin{array}{cccc} X & X & R & X \\ | & | & | & | \\ X-Si-X & R-Si-X & R-Si-X & X-Si-X \\ | & | & | & | \\ R & R & R & X \\ (I) & (II) & (III) & (IV) \end{array}$$

to hydrolyze and interconnect. The process is preferably conducted in the presence of a water miscible solvent in which the silane(s) are dissolved. The reaction is also preferably carried out by adding the water slowly or in a fine stream to the silane starting material. The use of a water miscible solvent, and controlled addition of the water, assists in maintaining homogeneity during hydrolysis.

The amount of water employed is preferably the calculated amount required for complete hydrolysis of the hydrolyzable groups (represented by X in the above formulas) present in the silane(s) to be reacted. The amount of solvent is not critical. Generally, from two to four volumes of solvent are used. The solvent can be an alcohol, an ether, a ketone, or an acid, an amide or the like. Typical solvents are methanol, ethanol, dioxane, acetone, acetic acid, and dimethyl formamide. Dioxane is a preferred solvent for silanes in which the hydrolyzable groups are halogen. Alcohols are preferred solvents when the hydrolyzable groups are alkoxides.

For the purpose of this invention, "hydrolyzable groups" mean any group or groups which react with water under the reaction conditions employed. They may be selected from hydrogen, halogen, alkoxide, and similar radicals. Preferably they are alkoxides wherein the alkyl group is a hydrocarbyl radical, i.e., a radical solely composed of carbon and hydrogen. Preferably, the alkoxide groups have up to about 4 carbon atoms.

The process may be carried out in the presence of a catalyst, e.g., an acid, or base. Acids suitable for this purpose have a $pK_a$ of less than or equal to 5. Preferably, they are volatile acids such as hydrochloric acid and acetic acid. Inorganic bases such as NaOH, KOH, and $Ca(OH)_2$, and organic bases such as lower alkylamines, e.g., triethylamine, can be used. Acids are preferred catalysts.

The process may be conducted at a temperature of from about $-25°$ C. to about $130°$ C. A preferred temperature range is from about $20°$ C. to about $65°$ C. The process is preferably conducted at ambient pressure; however, slightly greater or lesser pressures can be used if desired. In general, the process is complete in less than 24 hours. A preferred reaction time is from about 0.5 to about 5.0 hours. It is to be understood that the reaction time is not a truly independent variable but is dependent to at least to an appreciable extent on the other reaction conditions employed. For example, higher temperatures and more reactive hydrolyzable groups favor shorter reaction times. Less reactive groups and lower temperatures generally require longer reaction times.

The reactants and process conditions for the hydrolysis/condensation reaction discussed above, are discussed in more detail in application Ser. No. 300,094 filed Jan. 19, 1989, on the same day of this application, on behalf of William E. Pascoe and Bradley K. Coltrain for ORGANIC MODIFIED SILICIC ACID HETEROPOLYCONDENSATES. The disclosure of that application is incorporated by reference herein as if fully set forth.

As indicated above, this invention comprises a method for determining the presence of oxygen in a sample. This method comprises providing a membrane containing luminescent material which luminesces when excited by visible or ultraviolet light, and whose luminescence (intensity or lifetime) is quenchable by oxygen. The method is not restricted to any specific type of luminescence. Thus, the process of this invention can be based on photoluminescence, chemiluminescence, or thermoluminescence. The luminescent substance employed is incorporated in a silicic acid heteropolycondensate produced by the process discussed above. The heteropolycondensate/luminescent composite is exposed to the sample such that oxygen permeates the heteropolycondensate an quenches the luminescence of the indicator. The degree of quenching, i.e., the amount of quench by oxygen, is measured and used to determine the amount of oxygen in the sample.

The method of incorporating the luminescent compound in the heteropolycondensate is not critical. One method for doing so is set forth in the Examples below The sensor made from the heteropolycondensate/luminescent compound composite can be incorporated in a variety of sensing devices known in the art. Thus, the sensors of this invention may be used in the apparatus and methods set forth in:

Hirschfeld et al; *Journal of Lightwave Technology*, Vol. LT-5 No.7 (July 1987), pp. 1027-1032.

Gehrich et al; *IEEE Transactions on Bromedical Engineering*, Vol. BME-33 No. 2 (February 1986), pp. 117-132

Wolfbeis et al; *Mikrochimica Acta* [Wien] (1984), pp. 153-158.

Ruzicka et al; *Analytica Chimica Acta* 69, (1974), pp 129-141.

Wolfbeis et al; *Anal. Chem.* (1985) 57. pp. 2556-2561.

The luminescent compound employed in the sensors provided by this invention can be selected from a wide variety of luminescent materials known in the art. Typically, it may be acridine, pyrene, and the like, or the complex of platinum with octaethylporphyrin. Other suitable systems include the porphyrin, octaethylporphyrin, or phthalocyanine ligands complexed with $Cu^{++}$, $Zn^{++}$, $VO^{++}$, $Pd^{++}$, or $Pt^{++}$. Complexes of 1,10-phenanthroline, and substituted derivatives thereof, with chromium or a platinum subgroup metal can also be used. Typical luminescent materials which can be used in this invention are disclosed in British Patent 2,132,348B and in Lee et al; *Anal. Chem.* (1987) 59, pp. 279-283; and Avnir et al; *Journal of Non-Crystalline Solids* 74 (1985), pp. 395-406 (supra).

Generally, the concentration of the luminescent compound in the heteropolycondensate is within the range of from about 0.01 to about 0.4% by weight; more preferably from about 0.05 to about 0.2 weight percent.

EXAMPLE 1

The sol/gel (silicic acid heteropolycondensate) solutions were prepared by a standardized set of conditions as described below, using 80-phenyl/15-Ph$_2$/5-OSTEE as an example. In a 250 mL, three neck round bottom flask equipped with a mechanical stirrer and reflux condensor were placed 40 mL (0.17 mol) of phenyltriethoxysilane, 6.6 mL (0.031 mol) of dichlorodiphenylsilane, 2.3 mL (0.010 mol) of tetraethoxysilane, and 49 mL of ethanol. This mixture was stirred at 60° C. in a constant temperature bath while 10.8 mL (0.60 mol) of 0.15 M HCl was added dropwise. The resulting solution was stirred at 60° C. for one hour, allowed to stand overnight at ambient temperature, and then stirred an additional four hours at 60° C. (This process was not followed exactly in all cases. The reaction time was required to Produce materials with sufficient molecular weights that they could be isolated by a precipitation process. In general, three hours of stirring at 60° C. after addition of HCl was sufficient.)

The procedure described above could be easily modified to produce a variety of compositions simply by varying the monomers. The amount of ethanol which was added was equal in volume to the silane monomers. The amount of water added, in the form of 0.15M HCl, was equal to the number of moles of hydrolyzable groups on the silane monomers.

Since PtOEP is not soluble in ethanol, it was necessary to isolate the sol/gel polymers. This was done by pouring the sol/gel solutions prepared as described above into an excess of water. The polymer separated as a viscous oil which could be collected, dried in a vacuum oven, and dissolved in $CH_2Cl_2$ to 10% solids. This stock solution could then be used with PtOEP as described below.

When it is desired to endcap the polycondensate, an intermediate product can be prepared by polymerizing the silanes selected from compounds of Formulas I, II, or III, and then capping residual silanol groups with endcapping compounds of Formula IV, such as octadecyldimethylchlorosilane $(C_{18}H_{37})(CH_3)_2SiCl$. The amount of endcapping agent (in moles) is used in an amount within the range of from about 0.5 to about 8, more preferably from about 2 to about 4.

The temperature and reaction time employed for the endcapping can be within the ranges of from about 25° C. to about 100° C., and from about 0.25 to about 4.0 hours, respectively, more preferably from about 40° C. to about 70° C., and from about 0.5 to about 2 hours.

Non-endcapped or endcapped heteropolycondensates made according to the process illustrated by this Example can be upgraded by heating them at an elevated temperature and pressure as (discussed above and) illustrated by the following Example:

EXAMPLE 2

Phenyltriethoxysilane (60 ml, 0.25 mol) was polymerized according to the procedure set forth in Example 1 using 46.7 ml of ethanol and 13.4 ml (0.75 mol) of water. No acid catalyst was employed.

The ethanolic solution of the silicic acid heteropolycondensate produced was transferred to a stainless steel reaction vessel and dried by heating above the critical temperature of ethanol.

This was accomplished by raising the temperature of the solution at a rate of 100° C./hr. to 280° C. and a pressure of 2000 psi. At that point the reactor was vented and swept with nitrogen. The product was allowed to slowly cool to ambient temperature over a time span of about 16 hours.

The phenyl group containing silicic acid was in the form of a white powdery material which was soluble in methylene chloride.

EXAMPLE 3

Stock solutions were prepared by dissolving one gram of organic modified silicic acid heteropolycondensates in 10 mL of $CH_2Cl_2$ in which one milligram of PtOEP was added. Light was excluded from the stock solution. In this study, an optical fiber spectrometer (Guided Wave Model 200) was used to measure the phosphorescence intensity. This commercial instrument is equipped with a bifurcated fiber with one input fiber in the center axis to guide light to the sample and six output fibers along the edge to collect the scattered light and guide it back to the spectrometer. The fibers are terminated in a stainless steel probe. A polycarbonate or polymethylmethacrylate barrel was screwed on the probe, and a circular glass disc was glued to the barrel with dichloromethane. The 25 mil thick plate places the dye in the cross section of the exciting beam and the field of view defined by the numerical aperture of the optical fibers, maximizing the observable phosphorescence. The PtOEP/sol gel was first drop coated on the circular glass plate. This coating was then heated at 60° C. to 120° C. for one to four hours. After cooling to room temperature, this glass plate was "glued" to the barrel. During the measurement, the fiber was kept in a glass bottle which is connected to two flowmeters. The two flowmeters were used to control the ratio of compressed nitrogen and air partial pressure, while keeping the total pressure constant. The dye/polymer was excited with a tungsten lamp and an Ealing interference filter which passed wavelengths <550 nm. The phosphorescence was monitored at 642 nm with a bandwidth of 10 nm. Phosphorescence lifetimes were estimated from the recorded decay curves (which were obtained by time resolved phosphorescence) by nonlinear curve fitting. Visible absorption spectra were taken with an HP-4850A UV-VIS spectrometer.

FIG. 1 shows the results of the phosphorescence intensities of PtOEP incorporated in (X), 95-Phenyl/5-OSTEE and (O), Phenyl/propyl coatings, which were normalized with their corresponding intensities measured in nitrogen, as a function of time (in minutes). In this figure, each step change in the intensity is due to the change of the ratio of nitrogen to oxygen partial pressure by manually adjusting flowmeters. The measurements were done by increasing oxygen partial pressure in five steps from nitrogen to air. The phosphorescence intensity decreased as the oxygen partial pressure increased due to the quenching of phosphorescence by oxygen. When switching back to nitrogen, the intensity almost regains its original high value as shown in the case of (O), Phenyl/propyl. The slight decrease in the intensity when switching back and forth between nitrogen and air could arise from the instability of incorporated PtOEP, which will be discussed later. The response time of this sensor, depending on the coating thickness, could be in the range of seconds (e.g., 10–40 second). The difference in the change in intensity for each step change of oxygen partial pressure is significant between 95 Phenyl/5 OSTEE and phenyl/propyl. This difference is an indication of the differences in the oxygen permeability between these two coatings. Phenyl/propyl coatings show higher oxygen permeability than 95-Phenyl/5 OSTEE.

Figure 2:
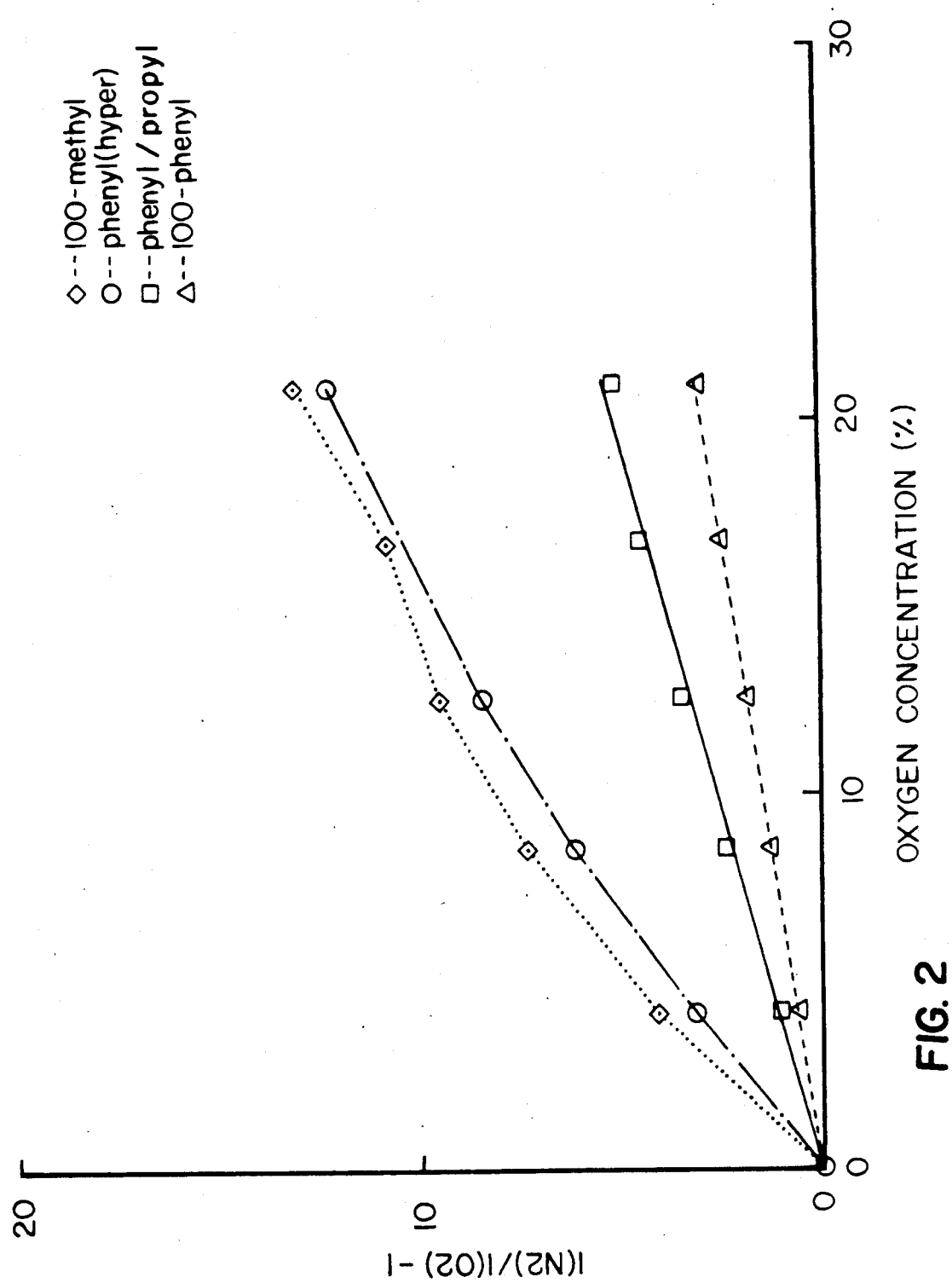
FIG. 2 to 4. A collection of plots of $[I(N_2) / I(O_2) - 1]$ as a function of oxygen concentration for various sol/gel coatings.
Figure 3:
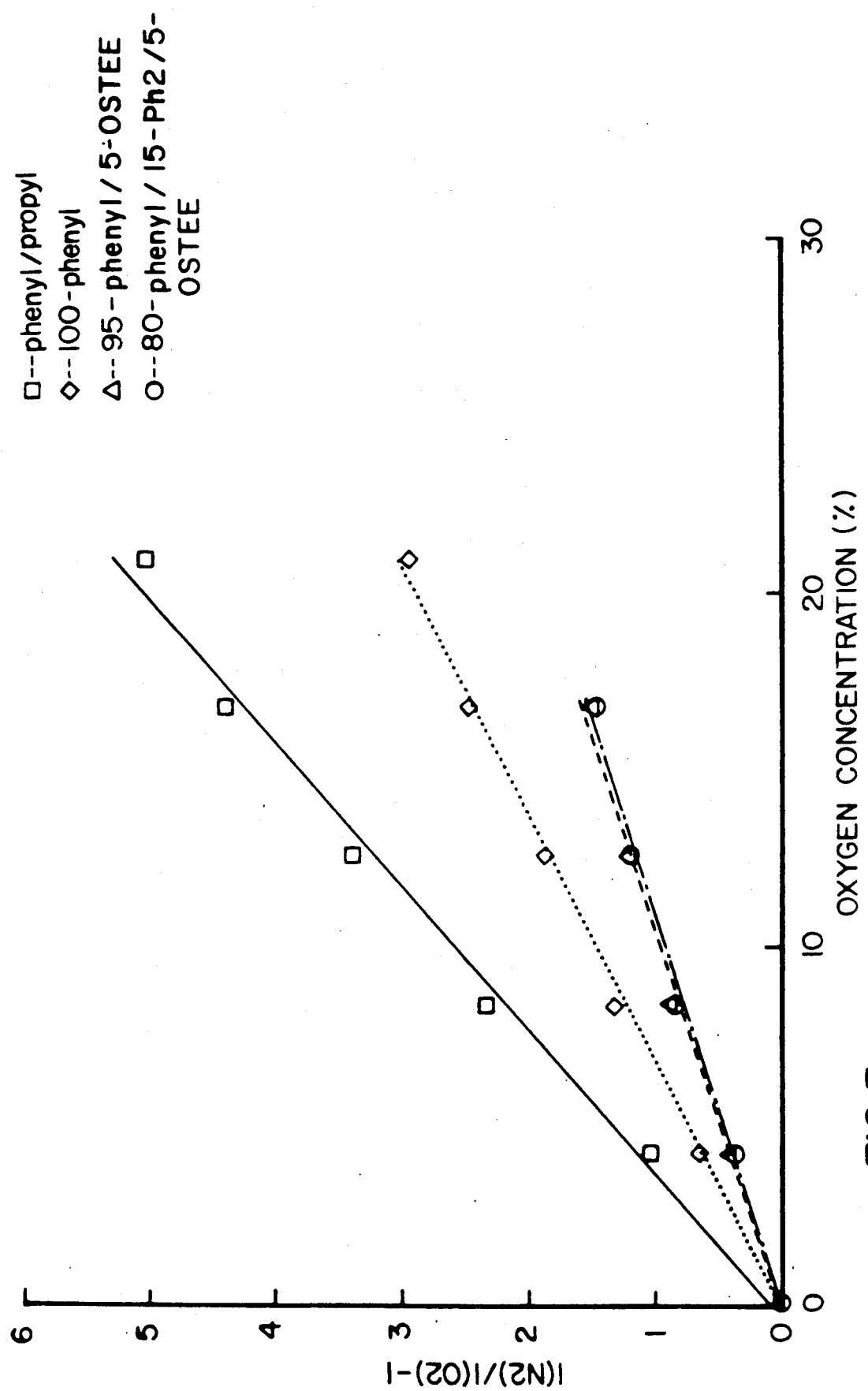
Figure 4:
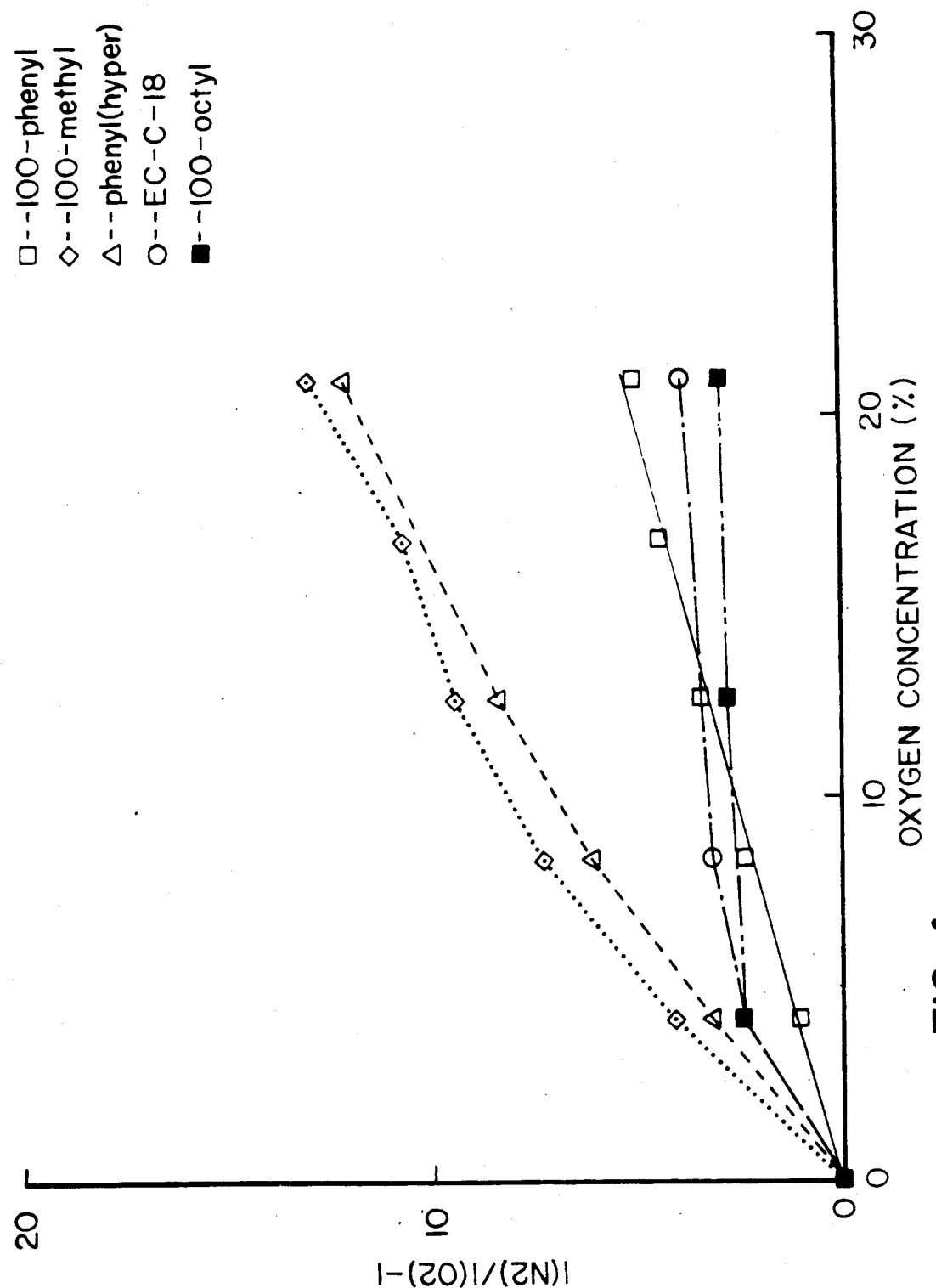

The slope of a plot of $[I(N_2)/I(O_2)-1]$ vs. $p_{O2}$ is proportional to the product of the lifetime $\tau_l$ and the permeability $P_{O2}$. FIGS. 2 to 4 are a collection of these plots for eight different sol/gel coatings. Their compositional differences have been described above. FIG. 2 shows that 100 methyl and phenyl(hyper) are significantly more permeable to oxygen than phenyl/propyl and 100 phenyl. However, 100-methyl and phenyl(hyper) show nonlinear behavior. On the other hand, 100-phenyl and phenyl/propyl show relatively linear responses to the oxygen concentration range examined (FIG. 2).

When a small amount of OSTEE was added to prepare 95-Phenyl/5-OSTEE and 80-Phenyl/15-Ph$_2$/5-OSTEE, their associated permeabilities are lower than that of 100-phenyl, which is 100% of the phenyl substituted sol/gel. Note that 95-Phenyl/5-OSTEE and 80-Phenyl/15-Ph$_2$/5-OSTEE show similar oxygen permeabilities (FIG. 3).

FIG. 4 shows results obtained on coatings prepared from an endcapped sol/gel, EC-C-18, and from a 100% n-octyltriethoxysilane sol/gel, 100-octyl. The response of these two coatings to oxygen quenching are significantly different from other silicic acid heteropolycondensates coatings. It is obvious that these polycondensate coatings are very permeable to oxygen. Their response curves reach plateaus at relatively low oxygen concentration.

Figure 5:
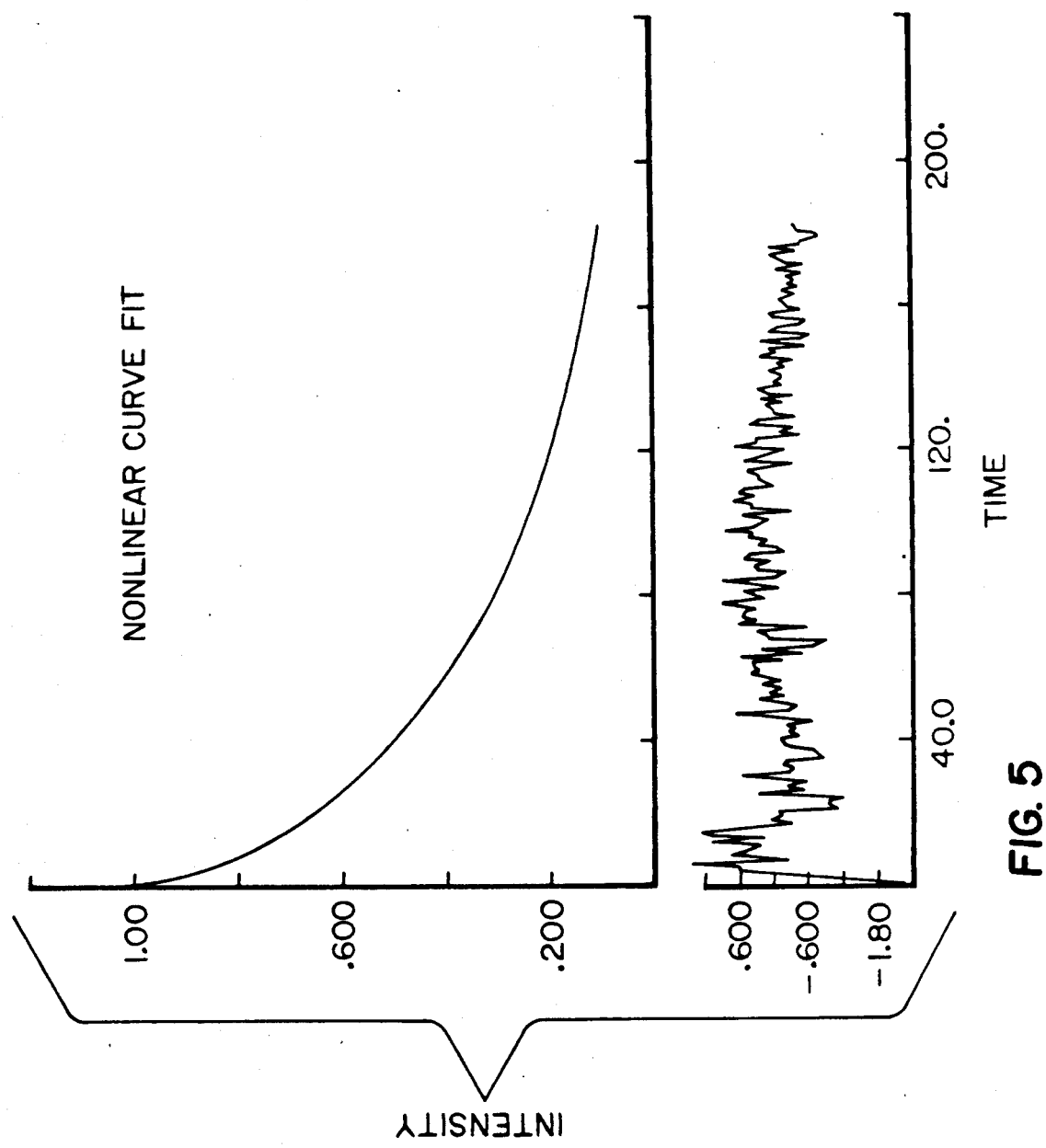
FIG. 5. Time resolved phosphorescence decay curve measured for a phenyl/propyl coating in nitrogen. The intensity has been normalized. The best fit curve is plotted on the top of the experimental data. The residuals are plotted below the decay curve and best fit curve.
Figure 6:
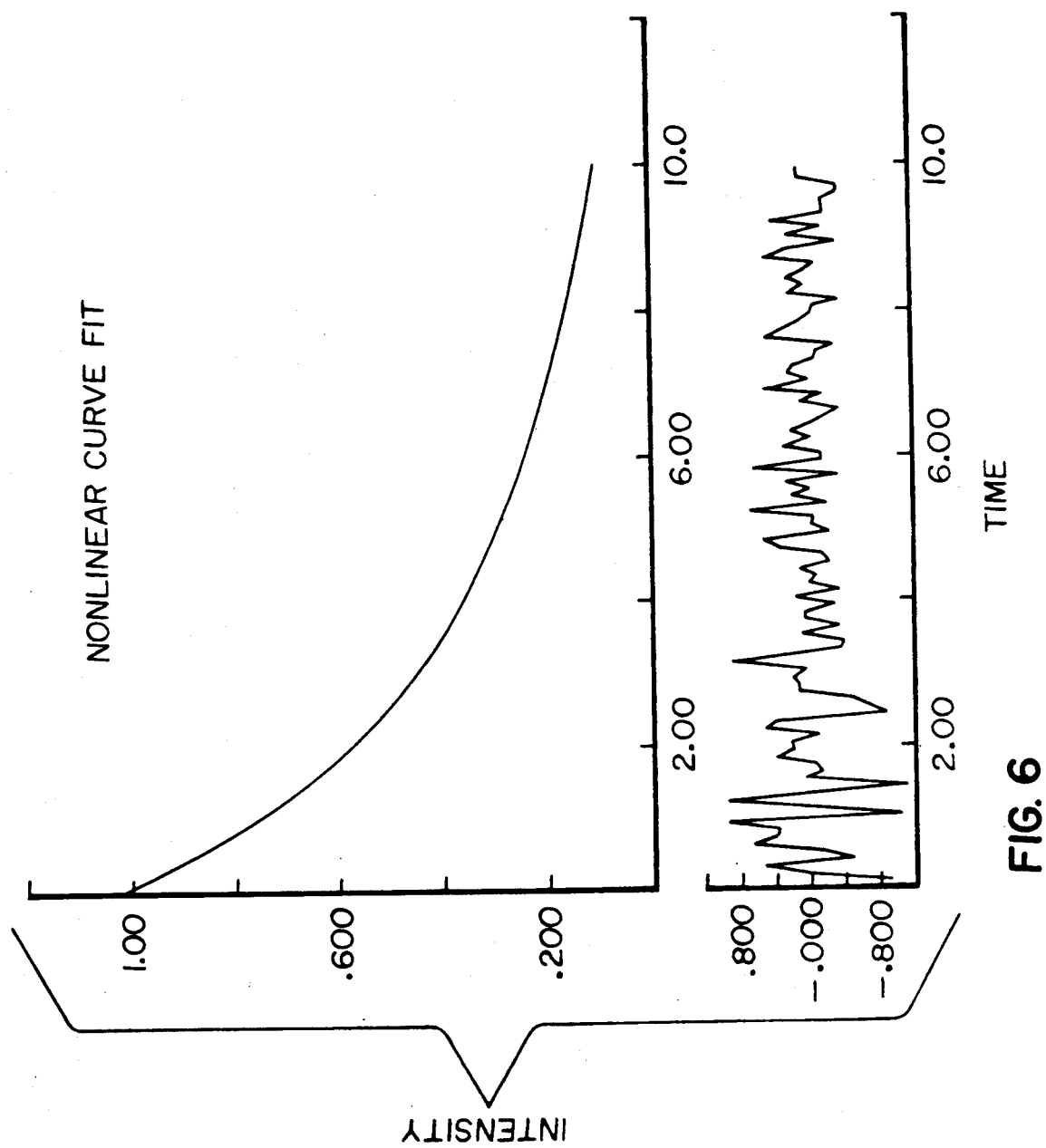
FIG. 6. The same experimental system as FIG. 5, except measured in air.

The measured oxygen permeability is also a function of the decay lifetimes of the phosphorescent probes. For a comparison of oxygen permeabilities among these coatings, we determined the associated phosphorescence lifetimes. The phosphorescence lifetimes of the incorporated PtOEP were evaluated from time resolved phosphorescence measurements. FIG. 5 shows a typical phosphorescence decay curve for a phenyl/propyl coating measured under nitrogen. It also includes a best fit-curve by assuming biexponential decay. The fit is reasonably good, a good fit having a low deviation and a random distribution in the residuals (residuals are plotted below the decay curves in FIGS. 5 and 6). The time scale is in microseconds. A biexponential fit might indicate that the excited triplet state of PtOEP experiences two different environments. FIG. 6 shows results obtained in air with the same coating used in FIG. 5. Again, this decay curve can be explained by two decay lifetimes which are shorter than those measured in nitrogen, as expected.

Table II summarizes the phosphorescence lifetimes measured both in air and nitrogen. This Table also includes the results measured for a PtOEP/CH$_2$Cl$_2$ solution.

TABLE II

| | PtOEP Phosphorescence Lifetimes* | | | |
|---|---|---|---|---|
| [N$_2$] | CH$_2$Cl$_2$ | Phenyl/ Propyl | 95-Phenyl/5-OSTEE | 100-Methyl |
| $\tau_{t1}$ | 12 | 13.7 | 18.2 | 18.7 |
| $\tau_{t2}$ | | 88.1 | 91.6 | 104.2 |
| [AIR] | | | | |
| $\tau_{ox1}$ | .46 | 2.0 | 3.5 | 2.6 |
| $\tau_{ox2}$ | | 5.2 | 7.5 | 5.3 |

*Time scale is in microseconds.

From FIGS. 2 to 4, the ratio of slopes, which are proportional to the product of the phosphorescence lifetime and the oxygen permeability, for 100-methyl:phenyl/propyl:95-Phenyl/5-OSTEE is 1:0.431:0.161. After correcting for the difference in their phosphorescence lifetimes, the ratio becomes 1:0.49:0.19. In this case, the luminescence lifetimes only change the relative magnitude, not the order, of the permeabilities among these three coatings.

Some conclusions can be made from the observed results. Alkyl substituted glassy coatings appear to be more permeable to oxygen than aryl substituted coatings. However, 100% phenyl substituted coatings prepared by hypercritical processing of Example 2 show much higher oxygen conventional low temperature sol/gel processes. If a portion of phenyl is substituted by propyl, it results in an increase in oxygen permeability. On the other hand, the introduction of 5% of OSTEE decreases the oxygen permeability. The OSTEE can cause the final structure of coatings to be more tightly cross-linked and will produce harder coatings.

As for endcapped sol/gel coatings, they show high oxygen permeability.

In a separate experiment, the oxygen permeability of sol/gel coatings prepared from aminopropylsilane was evaluated by measuring the phosphorescent spectra of incorporated PdTPPS both in air and nitrogen. The results show that air did not quench the phosphorescence of PdTPPS (palladium tetraphenylporphyrinsulfonate) to any appreciable amount. In other words, this coating is very impermeable to oxygen. This can be attributed to the characters of the amino groups. This kind of oxygen impermeable coating has its own value. For example, sol/gels containing aminopropyl groups can be blended with other sol/gels having greater oxygen permeability to fine tune the permeability of the sensor.

Figure 7A:
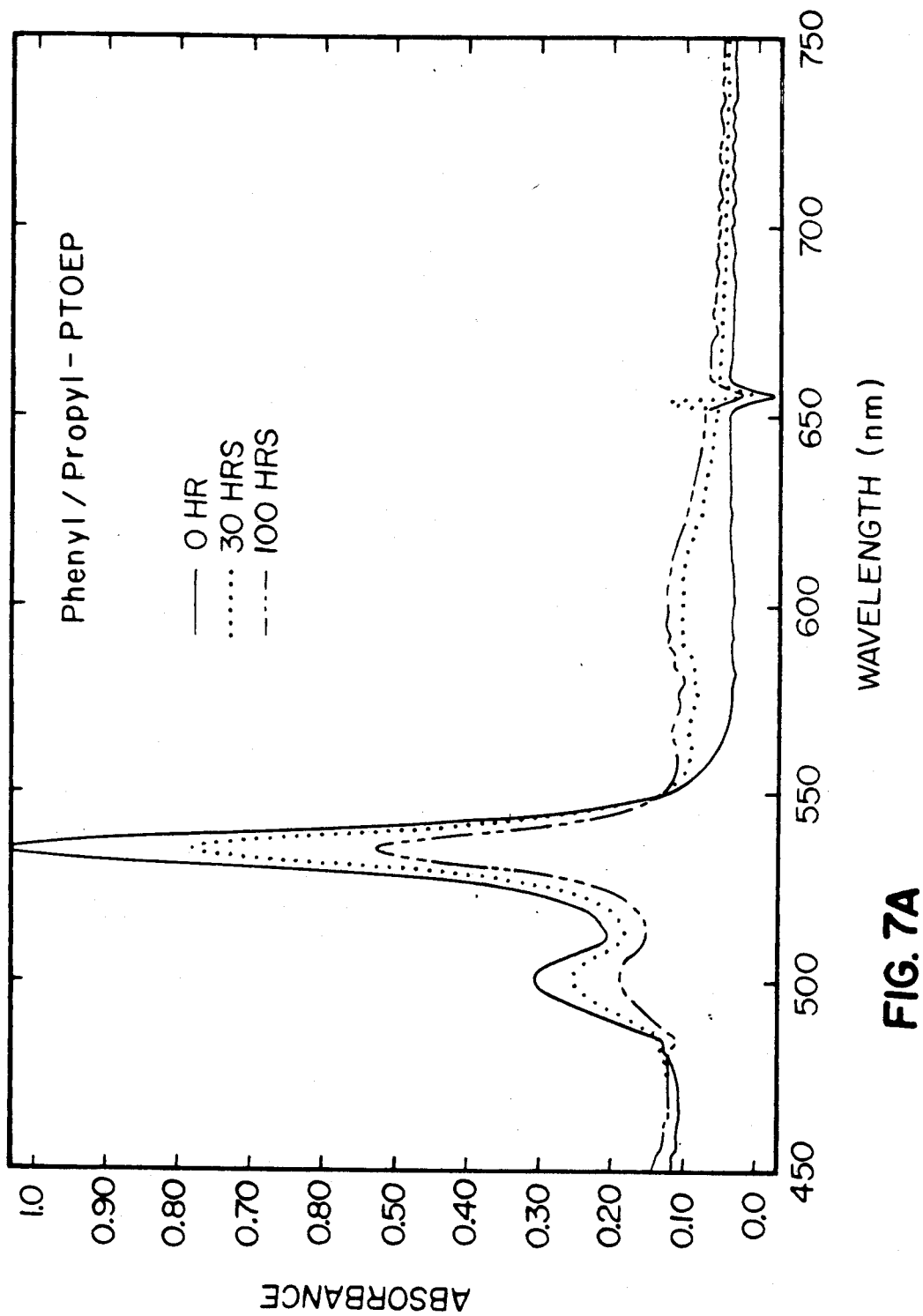
FIG. 7A,B. Visible absorption spectra of PtOEP in phenyl/propyl coatings measured at different exposure (air and room light) time (A) and (B) are without and with thermal pretreatment respectively.
Figure 7B:
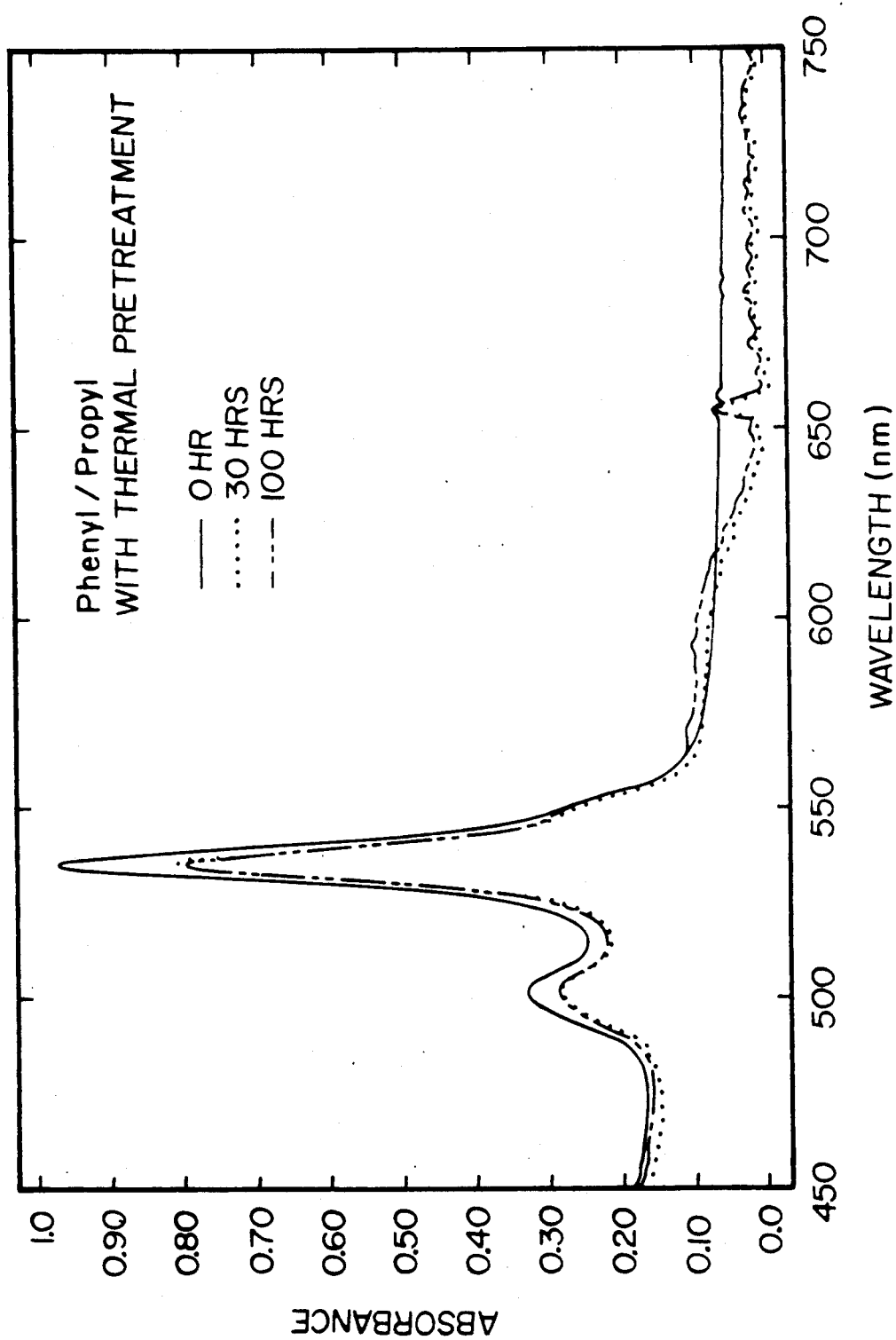

We observed that the phosphorescence intensities of incorporated PtOEP gradually decreased with time when exposed to light in air. In a controlled experiment, we have observed that both oxygen and light are required to cause this degradation. The visible spectra of PtOEP in phenyl/propyl coatings were monitored as a function of time. The results are presented in FIG. 7(A) (B), where (A) and (B) were obtained on coatings both without and with thermal pretreatment, respectively. The absorption intensities of PtOEP decrease significantly with time. The thermal pretreatment as shown in FIG. 7(B) seems to improve the stability to some extent.

We also observed that 100% phenyl sol/gel prepared from a hypercritical process showed a relatively slow photodegradation rate.

Despite the problem of dye stability, our work with sol/gels reported above has been shown to have many valuable properties as a coating for oxygen sensing. The mechanical and chemical stability of the sol/gel coating has allowed the sensor to be operated in 1N NaOH ferric oxyhydroxide aqueous slurries, latex colloidal suspensions, and gas, unlike other phosphorescent optrodes that have interference problems. The dynamic range is 3 to 4 times larger than the literature optrodes (Miller, F., et al, J. Lightwave Tech., Lt 5(7), 1027-1032, 1987) as illustrated by the curve for 100-methyl in FIG. 4. The optimum oxygen sensitivity range is tunable (as shown by FIGS. 4-6), and the lowest measurable oxygen concentration is <0.001%. The optical properties (transparency, scatter, etc.) of some sol/gel coatings approach those of optical quality glass.

It is to be understood that the materials of this invention need not be solely composed of silicic acid heteropolycondensates such as described above. They may also be modified to contain other metal oxide units in the polymeric matrix. For such modification, the raw material composition used in the preparative process of this invention may be modified to contain up to about 80 mole percent, and more preferably up to about 30 mole percent of one or more hydrolyzable materials, such as the alkoxides of titanium, molybdenum, lead, geranium, zirconium or vanadium. Modified condensates comprising metal oxide units derived from such materials have utilities similar to those discussed above.

A skilled practitioner, familiar with the above detailed description, can make modifications and substitutions without departing from the scope and spirit of the appended claims.

We claim:

1. A method of determining the presence of oxygen in a sample, said method comprising:
   (A) exposing a sensor to said sample, said sensor comprising:
      (i) a luminescent material which luminesces when excited by visible or ultraviolet light and whose lifetime or intensity of luminescence is quenchable by oxygen, and
      (ii) a membrane which is permeable to oxygen and in which said luminescent material is embedded,
   (B) allowing oxygen from said sample to permeate said membrane and contact said luminescent material,
   (C) measuring any quench-related decrease in luminescence caused by oxygen, and
   (D) using a measurement thereby obtained to determine the oxygen content of said sample;
   said membrane consisting essentially of an organic modified silicic acid heteropolycondensate having silane units with the formula RSi≡, such that the free valences of said formula are interconnected by oxygen and wherein R is a substituted or unsubstituted alkyl or aryl group.

2. A method of claim 1 wherein the R radicals in said silane units are selected from the group consisting of:
   (a) lower alkyl radicals and halosubstituted alkyl radicals having up to about 7 carbon atoms;
   (b) aryl radicals having up to about 14 carbon atoms; and
   (c) mixtures of (a) and (b).

3. A method of claim 2 wherein the R radicals in said silane units are selected such that from about 70 to 100% of said groups are selected from group (b) and 0–30% from group (a).

4. A method of claim 3 wherein said R radicals in said silane units are phenyl.

5. A method of claim 2 wherein said R radicals in said silane units are selected from subgroup (b), and said heteropolycondensate is further characterized by being substantially free of hydrolyzable or silanol groups.

6. A method of claim 5 said R radicals in said silane units are phenyl.

7. A method of claim 1 wherein the R radicals in said silane units are selected from the group consisting of alkyl groups and halosubstituted alkyl groups having from about 7 to about 20 carbon atoms.

8. A method of claim 7 wherein the R radicals in said silane units are octyl.

9. A method of claim 1 wherein R is selected from the group consisting of alkyl groups and halosubstituted alkyl groups of up to about 20 carbon atoms and aryl groups of up to about 14 carbons substituted with an amine radical —NRhd 1R$_2$ wherein R$_1$ and R$_2$ are alike or different and selected from the group consisting of hydrogen and lower alkyl groups having up to about 4 carbon atoms.

10. The method of claim 9 wherein R is aminopropyl.

11. A sensor comprising a luminescent material which luminesces when excited by visible or ultraviolet light and whose lifetime or intensity of illumination is quenchable by oxygen, said luminescent material being incorporated within a membrane consisting essentially of a silicic acid heteropolycondensate having silane units with the formula RSi≡ wherein the unsatisfied valences of said units are interconnected by oxygen and wherein R is a substituted or unsubstituted alkyl or aryl group.

* * * * *